(12) United States Patent
Knight

(10) Patent No.: US 7,862,539 B2
(45) Date of Patent: Jan. 4, 2011

(54) SYSTEM AND METHOD FOR INFUSING TOXINS USING SAFETY SET, CONNECT SET AND CYTO ADMIN SET

(75) Inventor: Thomas F. Knight, Trabuco Canyon, CA (US)

(73) Assignee: Codan US Corporation, Santa Ana, CA (US)

( * ) Notice: Subject to any disclaimer, the term of this patent is extended or adjusted under 35 U.S.C. 154(b) by 1237 days.

(21) Appl. No.: 11/446,446

(22) Filed: Jun. 1, 2006

(65) Prior Publication Data

US 2007/0282278 A1 Dec. 6, 2007

(51) Int. Cl.
*A61M 37/00* (2006.01)
*A61M 31/00* (2006.01)
*A61M 5/00* (2006.01)

(52) U.S. Cl. ............... 604/88; 604/82; 604/508; 604/262

(58) Field of Classification Search ............... 600/3–5, 600/12, 420, 431–433; 604/80, 83, 85, 88, 604/89, 91, 183, 184, 204–206, 257–259, 604/519, 520, 408–416, 506–508, 82, 262
See application file for complete search history.

(56) References Cited

U.S. PATENT DOCUMENTS

| 3,468,309 | A | | 9/1969 | Drewe |
|---|---|---|---|---|
| 5,122,123 | A | | 6/1992 | Vaillancourt |
| 5,250,037 | A | | 10/1993 | Bitdinger |
| 5,897,526 | A | * | 4/1999 | Vaillancourt ............... 604/82 |
| 5,899,888 | A | * | 5/1999 | Jepson et al. ............... 604/201 |
| 6,238,374 | B1 | | 5/2001 | Winkler |
| RE037,908 | E | | 11/2002 | Kinsey |
| 6,599,273 | B1 | | 7/2003 | Lopez |
| 6,726,672 | B1 | | 4/2004 | Hanly et al. |
| 6,755,804 | B2 | | 6/2004 | Crawford |
| 6,773,673 | B1 | | 8/2004 | Layfield et al. |
| 6,837,872 | B2 | | 1/2005 | Crawford |
| 6,902,207 | B2 | | 6/2005 | Lickliter |
| 2002/0189712 | A1 | * | 12/2002 | Safabash ............... 141/329 |
| 2004/0123758 | A1 | | 7/2004 | Shields |
| 2004/0254525 | A1 | | 12/2004 | Uber, III et al. |

\* cited by examiner

*Primary Examiner*—Kevin C Sirmons
*Assistant Examiner*—Catherine N Witczak
(74) *Attorney, Agent, or Firm*—David E. Heisey; Sheppard Mullin Richter & Hampton LLP

(57) ABSTRACT

The present invention provides a method for safely infusing a toxic fluid into a patient comprising the steps of drawing toxic fluid from a toxic fluid container into a withdrawing syringe, disconnecting a safety set from the toxic fluid container at a junction of a first male locking connector and ar interlocking slide, pushing the interlocking slide into a needle shroud assembly such that a sharpened distal tip of the needle is positioned within a resilient septum carried by the interlocking slide, connecting a second male locking connector to the interlocking slide, connecting the second male locking connector to a connect set, dispensing the toxic fluid from the syringe into the infusion bag, withdrawing the needle to position its sharpened distal tip within the resilient septum, attaching the connect set to the cyto admin set and infusing the toxic fluid into the patient.

18 Claims, 4 Drawing Sheets

Figure 1:
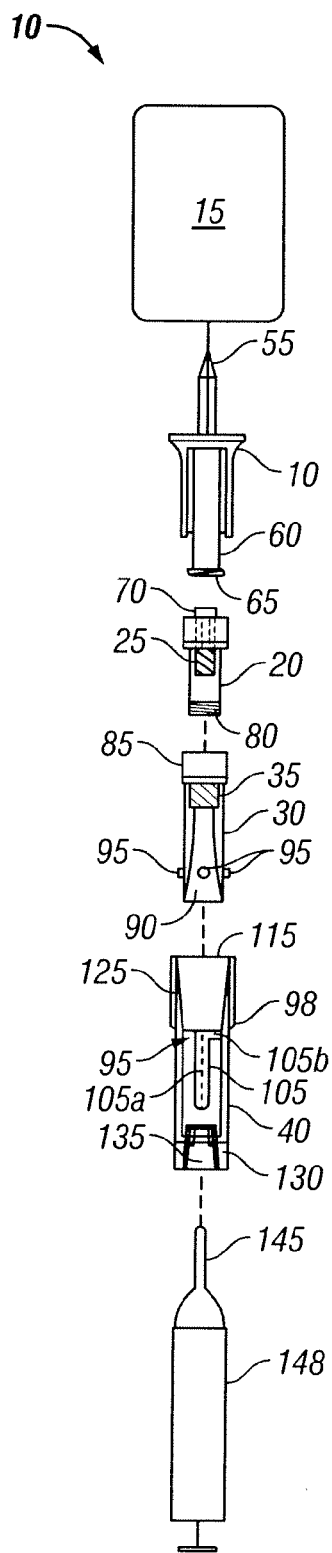
Figure 2:
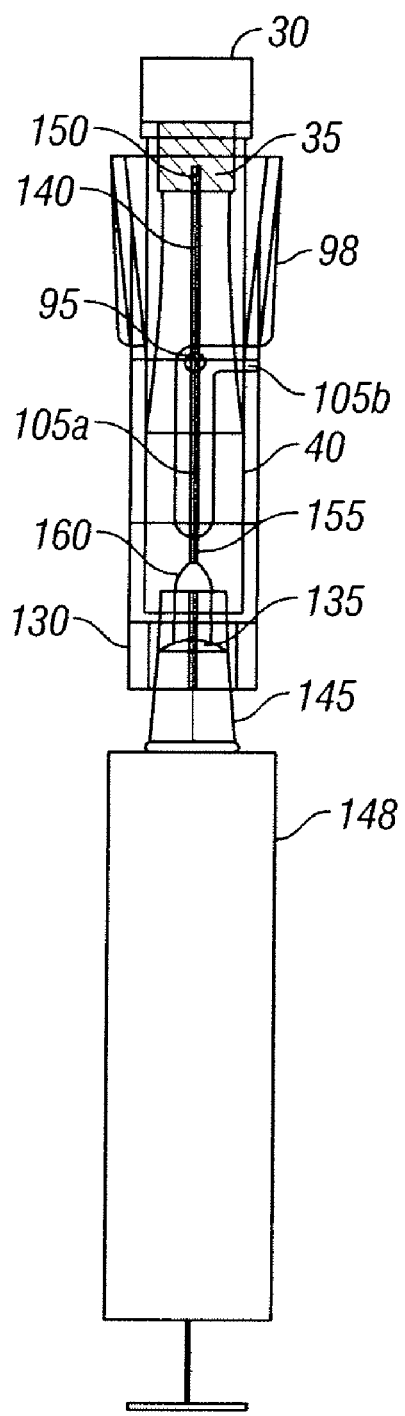

SYSTEM AND METHOD FOR INFUSING TOXINS USING SAFETY SET, CONNECT SET AND CYTO ADMIN SET

FIELD OF THE INVENTION

The invention broadly relates to a system and method for safely infusing toxins and more particularly to a system and method for enabling toxic solutions such as used in chemotherapy to be safely infused into a patient using a safety set, a connect set and a cyto admin set, with a significantly reduced risk of contacting the patient or the handler(s) performing the infusion

BACKGROUND OF THE INVENTION

Many medical applications involve the infusion of dangerous medicines such as toxic solutions, radioactive fluid or other dangerous fluid into a patient's body. These dangerous medicines include chemotherapy, biologically active substances, radiosensitizers and cytotoxics, which may be infused directly into a patient through an intravenous tube. Other medical applications involve infusing the fluid to a medical device located within or in proximity to the patient. In the case of toxic fluid syringe injections, current methods of syringe shielding may not provide the patient or the handler with the total protection needed in terms of radiation shielding or containment of a spill or leak of the infusion system.

In a typical application, toxic fluid are supplied to a patient via a delivery system, and then the delivery system is flushed with saline or some other non-hazardous dilutant. The infusion, removal and flushing of the radioactive fluid often results in the use of several syringes and fluid lines that must be interchanged in the infusion system with a resulting increase in the possibility that toxic fluid will leak or spill, thereby contaminating the surrounding environment. Syringe shields are currently available and are generally made to shield a syringe filled with toxic fluid by employing lead as a means of shielding against toxic radioactivity. However, these devices protect patients and handlers from radioactive fluid rather than containment of potential leaks or spills of toxic fluid.

In view of the above, there exists a need for a system and method for enabling toxic solutions such as used in chemotherapy to be safely infused with a significantly reduced risk of contacting the handler(s) performing the infusion.

SUMMARY OF THE INVENTION

In view of the foregoing, it is an object of the present invention to provide a system and method for enabling toxic solutions such as used in chemotherapy to be safely infused with a significantly reduced risk of contacting the handler(s) performing the infusion.

One aspect of the invention involves a method for safely infusing a toxic fluid into a patient using a safety set, a connect set and a cyto admin set, the safety set comprising a first male locking connector having a proximal end and a distal end attached to a toxic fluid container, an interlocking slide having a proximal end and a distal end that is releasably attached to the proximal end of the first male locking connector, a needle shroud assembly containing a needle and having a proximal end and a distal end slidably attached to the proximal end of the interlocking slide, and a withdrawing syringe having a distal tip releasably attached to the proximal end of the needle shroud assembly, the connect set comprising a connect set line in fluid communication with an infusion bag, wherein the connect set includes a port for connection with the safety set such that the withdrawing syringe is in fluid communication with the infusion bag, the cyto admin set comprising one or more check valves for connection with the connect set such that the infusion bag is in fluid communication with the cyto admin set, the method comprising the steps of drawing the toxic fluid from the toxic fluid container into the withdrawing syringe, disconnecting the safety set from the toxic fluid container at a junction of the first male locking connector and the interlocking slide, pushing the interlocking slide into the needle shroud assembly such that a sharpened distal tip of the needle is positioned within a resilient septum carried by the interlocking slide, connecting a second male locking connector to the interlocking slide, connecting the second male locking connector to the connect set, dispensing the toxic fluid from the syringe into the infusion bag, withdrawing the needle to position its sharpened distal tip within the resilient septum, attaching the connect set to the cyto admin set and infusing the toxic fluid into the patient.

In the preferred method of the invention, the interlocking slide is pushed partially into the needle shroud assembly such that a sharpened distal tip of the needle is positioned within a septum carried by the male locking connector. In particular, the interlocking slide includes outwardly projecting pins that are received within corresponding slots of the needle shroud assembly. The interlocking slide is rotated relative to the needle shroud assembly such that it may be pushed fully into the needle shroud assembly to allow fluid communication between the syringe and the toxic fluid delivery system. After fluid delivery, the needle is withdrawn to position its sharpened distal tip within a septum carried by the male locking connector. According to the preferred embodiment, the distal end of the male locking connector is tapered and the proximal end of male locking connector is threaded for releasable connection with the interlocking slide. Additionally, the needle shroud assembly comprises a shroud that houses the needle and the proximal end of the needle shroud assembly includes a tapered and threaded lock for connection with the syringe. The male locking connector, interlocking slide and needle shroud assembly may comprise a molded thermoplastic or thermoset polymer material.

Another aspect of the invention involves a system for safely infusing a toxic fluid into a patient, comprising: a safety set comprising a first male locking connector having a proximal end and a distal end attached to a toxic fluid container, an interlocking slide having a proximal end and a distal end that is releasably attached to the proximal end of the first male locking connector, a needle shroud assembly containing a needle and having a proximal end and a distal end slidably attached to the proximal end of the interlocking slide, and a withdrawing syringe having a distal tip releasably attached to the proximal end of the needle shroud assembly; a connect set comprising a connect set line in fluid communication with an infusion bag, wherein the connect set includes a port for connection with the safety set such that the withdrawing syringe is in fluid communication with the infusion bag; and a cyto admin set comprising one or more check valves for connection with the connect set such that the infusion bag is in fluid communication with the cyto admin set, wherein the toxic fluid is drawn from the toxic fluid container into the withdrawing syringe, wherein the safety set is disconnected from the toxic fluid container at a junction of the first male locking connector and the interlocking slide, wherein the interlocking slide is pushed into the needle shroud assembly such that a sharpened distal tip of the needle is positioned within a resilient septum carried by the interlocking slide, wherein a second male locking connector is connected to the interlocking slide, wherein the second male locking connector is connected to the connect set, wherein the toxic fluid is dispensed from the syringe into the infusion bag, wherein the needle is withdrawn to position its sharpened distal tip within the resilient septum, wherein the connect set is attached to the cyto admin set the toxic fluid is infused into the patient.

BRIEF DESCRIPTION OF THE DRAWINGS

FIG. 1 is an exploded view which illustrates a safety set for withdrawing toxic fluid from a toxic fluid container and into a withdrawing syringe, in accordance with a preferred system and method of the present invention;

FIG. 2 is a side sectional view of the safety set of FIG. 1, wherein an interlocking slide is in mechanical engagement with a needle shroud assembly;

FIG. 3 is an exploded view that illustrates the safety set in fluid communication with an infusion bag and a connect set, in accordance with the preferred system and method of the present invention; and FIG. 4 is a side view that illustrates the infusion bag and connect set in fluid communication with a cyto admin set for infusing the toxic fluid into a patient, in accordance with the preferred system and method of the present invention.

DETAILED DESCRIPTION

In the following paragraphs, the present invention will be described in detail by way of example with reference to the attached drawings. Throughout this description, the preferred embodiment and examples shown should be considered as exemplars, rather than as limitations on the present invention. As used herein, the "present invention" refers to any one of the embodiments of the invention described herein, and any equivalents. Furthermore, reference to various feature(s) of the "present invention" throughout this document does not mean that all claimed embodiments or methods must include the referenced feature(s).

FIG. 1 illustrates a safety set 10 for withdrawing toxic fluid from a toxic fluid container 15 and into a withdrawing syringe 148, in accordance with a preferred system and method of the present invention. The system and method described herein enables toxic fluid such as used in chemotherapy to be safely infused into a patient. Specifically, the safety set 10 comprises a vial spike 10 for penetrating the toxic fluid container 15 in order to withdraw the toxic fluid therefrom, a first male locking connector 20 having an elastomeric septum 25, an interlocking slide 30 having an elastomeric septum 35 and a needle shroud assembly 40. The vial spike 10 comprises a sharpened distal tip 55 for penetrating the toxic fluid container 15, a central lumen for the passage of fluid, and a proximal end 60 having an opening 65 for receiving a portion of the first male locking connector 20. The vial spike 10 preferably includes an inline filtration membrane within the central lumen that allows the toxic fluid to be filtered as it is withdrawn from the toxic fluid container.

With further reference to FIG. 1, the first male locking connector 20 includes a central lumen for the passage of fluid and a tapered distal end 70 that is inserted and force fit within the proximal opening 65 of the vial spike 10. The first male locking connector 20 further comprises a threaded proximal end 80 for releasable connection with corresponding threads (not shown) within a distal end 85 of the interlocking slide 30. When the first male locking connector 20 is connected with the interlocking slide 30, the joint between these components is sealed from the external environment by the elastomeric septum 25 and the elastomeric septum 35. The septa 25, 35 also act as a seal for the open end of a needle disposed within a central lumen of the interlocking slide 30. It is preferred that the septa 25, 35 comprise an elastomeric material that allows needle penetration through the length of the septa, and further allows the needle to be easily withdrawn from the septa. In addition, the septum 25 within the first male locking connector 20 preferably maintains complete seal integrity with respect to the central lumen of the first male locking connector 20 after withdrawal of the needle. The first male locking connector 20 may comprise a molded thermoplastic or thermoset polymer material.

A proximal end 90 of the interlocking slide 30 includes a plurality of outwardly projecting pins 95 dimensioned to be received within corresponding slots 105 within the needle shroud assembly 40, thereby forming a mechanical slide. The interlocking slide septum 35 preferably maintains complete seal integrity with respect to the external environment and the central lumen of the interlocking slide 30 after withdrawal of the needle. Similar to the first male locking connector 20, the interlocking slide 30 may comprise a molded thermoplastic or thermoset polymer material. The needle shroud assembly 40 comprises a shroud 98 that houses the needle, the shroud 98 comprising a molded thermoplastic or thermoset polymer material. As described above, the needle shroud assembly 40 also comprises slots 105 for receiving pins 95 of interlocking slide. In particular, the proximal end 90 of the interlocking slide 30 fits within an opening 115 within a distal end 125 of the needle shroud assembly 40. Additionally, a proximal end 130 of the needle shroud assembly 40 includes a tapered and threaded lock 135 for connection with a distal tip 145 of a standard luer locking syringe 148 or other conventional fluid withdrawing device. The syringe 148 is employed to withdraw a predetermined amount of toxic fluid from the toxic fluid container 15.

Referring to FIG. 2, the interlocking slide 30 is depicted in mechanical engagement with the needle shroud assembly 40. In particular, the needle shroud assembly 40 contains the needle 140 having sharpened distal end 150 and non-sharpened proximal end 155. The distal tip 145 of the withdrawing syringe 148 is shown in locking engagement with the tapered and threaded lock 135 at the proximal end 130 of the needle shroud assembly 40, such that the needle 140 is in fluid communication with the syringe 148. The needle 140 preferably comprises a hollow metallic or polymer cannula that is sharpened at the distal end 150 to allow for clean and easy penetration through both the interlocking slide septum 35 and the male locking connector septum 25. The needle 140 may be attached to an inside diameter of the shroud 98 by way of a metallic or polymer hub 160, which is adhesively bonded, potted and/or joined by mechanical compression with a non-sharpened proximal end 155 of the needle 140. Similarly, the hub 160 may be bonded, potted and/or joined by mechanical compression to an inside diameter of the shroud 98. After drug withdrawal, the system is disconnected from the toxic fluid container 15 at the junction of the first male locking connector 20 and the interlocking slide 30. Specifically, the first male locking connector 20 remains attached to the vial spike 10 and the toxic fluid container 15, such that the first male locking connector 20 functions as a seal for the partially or fully emptied toxic fluid container 15.

FIG. 3 illustrates the withdrawing syringe 148 of the safety set 10 in fluid communication with an infusion bag 186 and a connect set 170. In particular, after disconnecting the system from the toxic fluid container 15 at the junction of the first male locking connector 20 and the interlocking slide 30, a second male locking connector 20' is then attached to the interlocking slide 30 by way of its threaded proximal end 80'.

Figure 3:
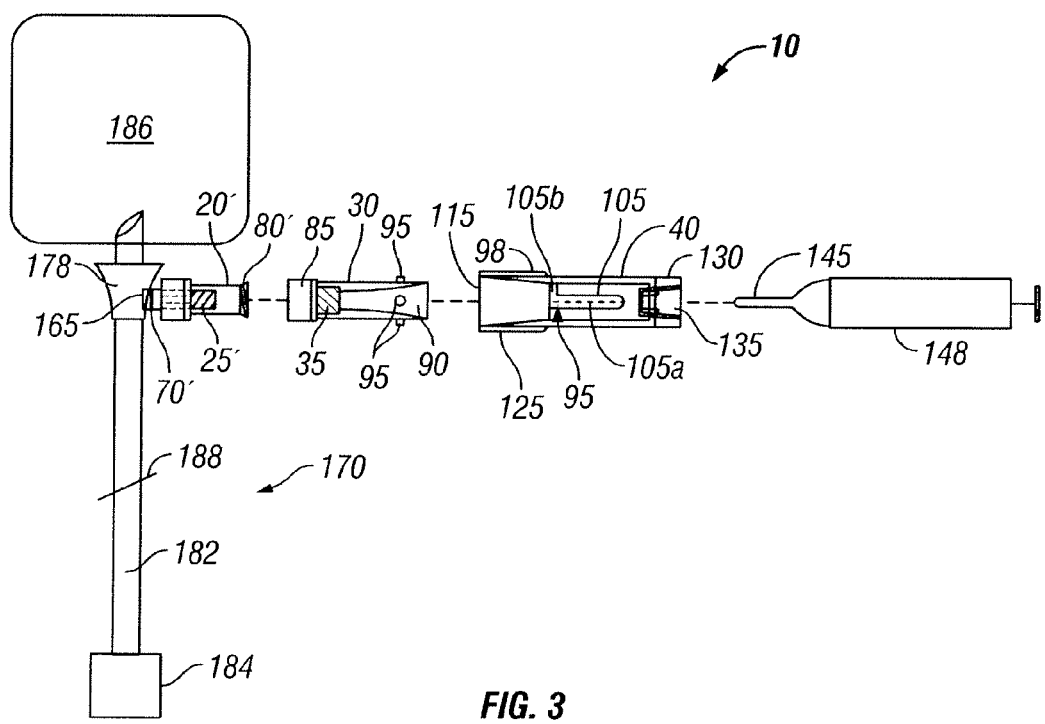

Similar to the first male locking connector 20, the second male locking connector 20' comprises an elastomeric septum 25', a tapered distal end 70' and a threaded proximal end 80', which is attached to the distal end 85 of the interlocking slide 30. The distal end 70' of the second male locking connector 20' is attached to a vial spike 178 of a connect set 170 by way of a drug entry port 165. The connect set 170 comprises a connect set line 182 connected at one end to an infusion bag 186 or other delivery system via the vial spike 178. The connect set 170 further comprises a clamp 188 and a spin lock 184 attached to the other end of the connect set line 182. As illustrated in FIG. 3, the tapered distal end 70' of the second male locking connector 20' is attached in a conventional manner to the drug entry port 165 to allow the toxic fluid in the standard luer locking syringe 148 to be injected into the infusion bag 186. During this process, the clamp 188 is used to prevent any fluids from entering the connect set line 182.

Figure 4:
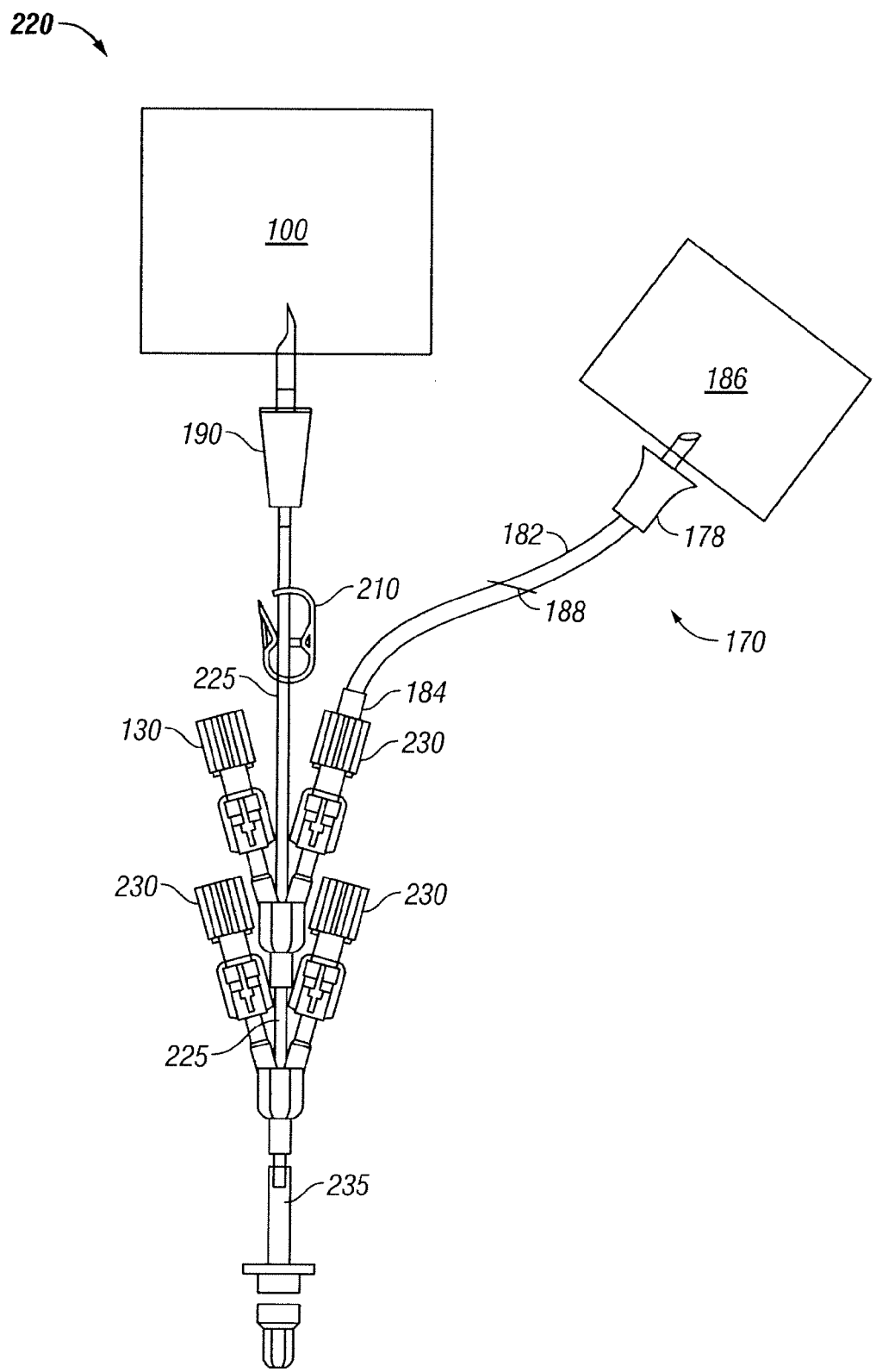

FIG. 4 illustrates the infusion bag 186 and connect set 170 in fluid communication with a cyto admin set 220 for infusing the toxic fluid into the patient. Specifically, after injecting the toxic fluid into the infusion bag 186, the connect set line 182 is connected to a cyto admin set 220 for the passage of fluids into the patient. The cyto admin set 220 comprises a one-way valve port 190 in fluid communication with an intravenous bag 200, a clamp 210, and a primary line 225 for the passage of saline or neutral fluids into the patient. The clamp 210 is used to obstruct the primary line 225 while the toxic fluid is being infused into the patient. The cyto admin set 220 further comprises a plurality of check valves 230 and a dedicated universal spike adapter 235. In the illustrated embodiment, the cyto admin set 220 contains four check valves 230. However, as would be appreciated by those of skill in the art, the cyto admin set 220 may include any number of check valves 230 without departing from the scope of the present invention. The connect set 170 is attached to one of the check valves 230 via the spin lock 184 to permit fluid communication between the connect set 170 and the cyto admin set 220. By way of example, the other check valves 230 may be employed to selectively infuse other solutions into the patient on an as needed basis.

Once fluid communication is established, the toxic fluids within the infusion bag 186 are infused into the patient by way of the connect set line 182, the check valve 230 and the dedicated universal spike adapter 235. The spike adapter 235 preferably is configured to be connected with virtually any conventional spike on any pump set. The pump set, for example, may comprise a spike, a pump key, a length of tubing, a needleless y-site, a roller clamp, and a luer lock for attachment with an IV catheter that connects to the patient's blood vessel. Since the dedicated universal spike adapter 235 is compatible with existing pump equipment, the connect set 170 may be attached to the existing pump sets without affecting the overall function of the device.

In accordance with the principles of the present invention, a method for enabling a toxic fluid to be safely infused into a patient will now be described. With reference to FIGS. 1-4, the method comprises penetrating the toxic fluid container 15 using the vial spike 10 and drawing the toxic fluid from the toxic fluid container 15 into the standard luer locking syringe 148. After drug withdrawal, the system is disconnected from the toxic fluid container 15 at the junction of the male locking connector 20 and the interlocking slide 30. Specifically, the first male locking connector 20 remains attached to the vial spike 10 and the toxic fluid container 15, such that first male locking connector 20 functions as a seal for the toxic fluid container 15. The next step comprises pushing the interlocking slide 30 into the needle shroud assembly 40 guided by the outwardly projecting pins 95 that are received within the corresponding slots 105 having longitudinal portions 105a and cross-slot portions 105b. More particularly, the interlocking slide 30 is pushed into the needle shroud assembly 40 until the pins 95 abut the cross-slot portions 105b. In this position, the sharpened distal tip 150 of the needle 140 is positioned substantially in the center of the resilient septum 25 carried by the interlocking slide 30, such that the syringe, the needle shroud assembly 40 and the interlocking slide 30 are safe to handle.

Referring to FIG. 3, the next step involves connecting the second male locking connector 20' to the interlocking slide 30 such that its threaded proximal end 80' is threadably attached to the distal end 85 of the interlocking slide 30. In the next step, the distal end 70' of the second male locking connector 20' is attached to the vial spike 178 of the connect set 170 by way of the drug entry port 165. In the subsequent step, the interlocking slide 30 is rotated relative to, and pushed fully into, the needle shroud assembly 40, thereby forcing the needle 140 through the resilient septum 25' carried by the second male locking connector 20'. Then, the toxic fluid is dispensed from the syringe 148 into the infusion bag 186. During this process, the clamp 188 is used to prevent any fluids from entering the connect set line 182. After delivery of the toxic fluid to the infusion bag 186, the needle 140 is withdrawn to position its tip within the interlocking slide septum 35 by withdrawing the interlocking slide 30 from the needle shroud assembly 40 until the pins 95 abut the cross-slot portions 105b.

Referring to FIG. 4, the next steps involve moving the connect set 170 to the vicinity of the patient and then attaching the connect set 170 to the cyto admin set 220. In particular, the connect set 170 is attached to one of the check valves 230 of the cyto admin set 220 via the spin lock 184 to permit fluid communication between the connect set 170 and the cyto admin set 220. The primary line 225 of the cyto admin set 220 for the passage of saline or neutral fluids into the patient may be clamped off (using clamp 210) while the toxic fluid is being infused into the patient. The subsequent steps entail removing the clamp 188 from the connect set line 182 to allow fluid flow from the infusion bag 186 to the patient and infusing the toxic fluid into the patient. After infusion of the toxic fluid, the clamp 210 may be removed from the primary line 225 such that the infusion of fluids from the intravenous bag 100 may be resumed.

Thus, it is seen that a system and method for safely infusing toxins is provided. One skilled in the art will appreciate that the present invention can be practiced by other than the various embodiments and preferred embodiments, which are presented in this description for purposes of illustration and not of limitation, and the present invention is limited only by the claims that follow. It is noted that equivalents for the particular embodiments discussed in this description may practice the invention as well.

The invention claimed is:

1. A method for safely infusing a toxic fluid into a patient using a safety set, a connect set and a cyto admin set, the safety set comprising a first male locking connector having a proximal end and a distal end attached to a toxic fluid container, an interlocking slide having a proximal end and a distal end that is releasably attached to the proximal end of the first male locking connector, a needle shroud assembly containing a needle and having a proximal end and a distal end slidably attached to the proximal end of the interlocking slide, and a withdrawing syringe having a distal up releasably attached to the proximal end of the needle shroud assembly, the connect set comprising a connect set line in fluid communication with an infusion bag, wherein the connect set includes a port for connection with the safety set such that the withdrawing syringe is in fluid communication with the infusion bag, the cyto admin set comprising one or more check valves for connection with the connect set such that the infusion bag is in fluid communication with the cyto admin set, the method comprising the steps of:

drawing the toxic fluid from the toxic fluid container into the withdrawing syringe;

disconnecting the safety set from the toxic fluid container at a junction of the first male locking connector and the interlocking slide;

pushing the interlocking slide into the needle shroud assembly such that one or more outwardly projecting pins of the interlocking slide are received within corresponding slots of the needle shroud assembly, and such that a sharpened distal tip of the needle is positioned within a resilient septum carried by the interlocking slide;

connecting a second male locking connector to the interlocking slide;

connecting the second male locking connector to the connect set;

dispensing the toxic fluid from. the syringe into the infusion bag;

withdrawing the needle to position its sharpened distal tip within the, resilient septum;

attaching the connect set to the cyto admin set; and infusing the toxic fluid into the patient.

2. The method of claim 1, wherein after disconnecting the safety set from the toxic fluid container at a junction of the first male locking connector and the interlocking slide, the first male locking connector remains attached to the toxic fluid container such that first male locking connector functions as a seal for the toxic fluid container.

3. The method of claim 1, wherein the slots include longitudinal portions and cross-slot portions.

4. The method of claim 1, wherein the step of connecting the second male locking connector to the interlocking slide involves threadably attaching a threaded proximal end of the second male locking connector to a distal end of the interlocking slide.

5. The method of claim 1, wherein the step of connecting the second male locking connector to the connect set comprises attaching a distal end of the second male locking connector to a vial spike of the connect set by way of a drug entry port.

6. The method of claim 5, wherein the step of connecting the second male locking connector to the connect set further comprises rotating the interlocking slide relative to, and pushing the interlocking slide into, the needle shroud assembly, thereby forcing the needle through a resilient septum carried by the second male locking connector.

7. The method of claim 1, wherein the step of attaching the connect set to the cyto admin set comprises attaching the connect set to a check valve of the cyto admin set to permit fluid communication between the connect set and the cyto admin set.

8. The method of claim 1, wherein a primary line of the cyto admin set is clamped off while the toxic fluid is being infused into the patient.

9. The method of claim 1, wherein the cyto admin set includes a dedicated universal spike adapter configured to be connected with a conventional spike on a conventional pump set.

10. The method of claim 9, wherein the conventional pump set comprises a spike, a pump key, a length of tubing, a needleless y-site, a roller clamp, or a luer lock for attachment with an IV catheter that connects to the patient's blood vessel.

11. The system of claim 1, wherein the cyto admin set includes a dedicated universal spike adapter configured to be connected with a conventional spike on a conventional pump set.

12. The system of claim 11, wherein the conventional pump set comprises a spike, a pump key, a length of tubing, a needleless y-site, a roller clamp, or a luer lock for attachment with an IV catheter that connects to the patient's blood vessel.

13. A system for safely infusing a toxic fluid into a patient, comprising:

a safety set comprising a first male locking connector having a proximal end and a distal end attached to a toxic fluid container, an interlocking slide having a proximal end and a distal end that is releasably attached to the proximal end of the first male locking connector, a needle shroud assembly containing a needle and having a proximal end and a distal end slidably attached to the proximal end of the interlocking slide, and a withdrawing syringe having a distal tip releasably attached to the proximal end of the needle shroud assembly;

a connect set comprising a connect set line in fluid communication with an infusion bag, wherein the connect set includes a port for connection with the safety set such that the withdrawing syringe is in fluid communication with the infusion bag; and a cyto admin set comprising one or more check valves for connection with the connect set such that the infusion bag is in fluid communication with the cyto admin set;

wherein the toxic fluid is drawn from the toxic fluid container into the withdrawing syringe;

wherein the safety set is disconnected from the toxic fluid container at a junction of the first male locking connector and the interlocking slide;

wherein the interlocking slide is pushed into the needle shroud assembly such that one or more outwardly projecting pins of the interlocking slide are received within corresponding slots of the needle shroud assembly, and such that a sharpened distal tip of the needle is positioned within a resilient septum carried by the interlocking slide;

wherein a second male locking connector is connected to the interlocking slide;

wherein the second male locking connector is connected to the connect set;

wherein the toxic fluid is dispensed from the syringe into the infusion bag;

wherein the needle is withdrawn to position its sharpened distal tip within the resilient septum;

wherein the connect set is attached to the cyto admin set the toxic fluid is infused into the patient.

14. The system of claim 13, wherein after disconnecting the safety set from the toxic fluid container at a junction of the first male locking connector and the interlocking slide, the first male locking connector remains attached to the toxic fluid container such that first male locking connector functions as a seal for the toxic fluid container.

15. The system of claim 13, wherein connecting the second male locking connector to the interlocking slide involves threadably attaching a threaded proximal end of the second male locking connector to a distal end of the interlocking slide.

16. The system of claim 13, wherein the step of connecting the second male locking connector to the connect set comprises attaching a distal end of the second male locking connector to a vial spike of the connect set by way of a drug entry port.

17. The system of claim 16, wherein connecting the second male locking connector to the connect set further comprises rotating the interlocking slide relative to, and pushing the interlocking slide into, the needle shroud assembly, thereby forcing he needle through a resilient septum carried by the second male locking connector.

18. The system of claim 13, wherein attaching the connect set to the cyto admin set comprises attaching the connect set to a check valve of the cyto admin set to permit fluid communication between the connect set and the cyto admin set.

\* \* \* \* \*